United States Patent
Marsh et al.

(10) Patent No.: US 11,458,085 B2
(45) Date of Patent: *Oct. 4, 2022

(54) HAIR CARE COMPOSITIONS FOR CALCIUM CHELATION

(71) Applicant: The Procter & Gamble Company, Cincinnati, OH (US)

(72) Inventors: Jennifer Mary Marsh, Deerfield Township, OH (US); Casey Patrick Kelly, Wyoming, OH (US)

(73) Assignee: The Procter and Gamble Company, Cincinnati, OH (US)

( * ) Notice: Subject to any disclaimer, the term of this patent is extended or adjusted under 35 U.S.C. 154(b) by 22 days.

This patent is subject to a terminal disclaimer.

(21) Appl. No.: 16/931,880

(22) Filed: Jul. 17, 2020

(65) Prior Publication Data

US 2020/0345607 A1 Nov. 5, 2020

Related U.S. Application Data

(63) Continuation of application No. 15/630,437, filed on Jun. 22, 2017, now abandoned.

(60) Provisional application No. 62/356,987, filed on Jun. 30, 2016.

(51) Int. Cl.
| | |
|---|---|
| *A61K 8/49* | (2006.01) |
| *A61K 8/24* | (2006.01) |
| *A61K 8/362* | (2006.01) |
| *A61Q 5/02* | (2006.01) |
| *A61K 8/04* | (2006.01) |
| *A61K 8/35* | (2006.01) |
| *A61K 8/365* | (2006.01) |
| *A61K 8/44* | (2006.01) |
| *A61K 8/46* | (2006.01) |
| *A61K 8/55* | (2006.01) |
| *A61Q 5/00* | (2006.01) |

(52) U.S. Cl.
CPC ............ *A61K 8/4946* (2013.01); *A61K 8/042* (2013.01); *A61K 8/24* (2013.01); *A61K 8/35* (2013.01); *A61K 8/362* (2013.01); *A61K 8/365* (2013.01); *A61K 8/44* (2013.01); *A61K 8/466* (2013.01); *A61K 8/49* (2013.01); *A61K 8/494* (2013.01); *A61K 8/55* (2013.01); *A61Q 5/006* (2013.01); *A61Q 5/02* (2013.01); *A61K 2800/51* (2013.01)

(58) Field of Classification Search
None
See application file for complete search history.

(56) References Cited

U.S. PATENT DOCUMENTS

| | | |
|---|---|---|
| 3,940,482 A | 2/1976 | Grand |
| 4,089,945 A | 5/1978 | Brinkman et al. |
| 4,185,106 A | 1/1980 | Dittmar et al. |
| 4,321,156 A | 3/1982 | Bushman |
| 4,412,943 A | 11/1983 | Hirota et al. |
| 4,749,507 A | 6/1988 | Varco |
| 4,822,604 A | 4/1989 | Knoll et al. |
| 4,855,130 A | 8/1989 | Konrad et al. |
| 5,306,489 A | 4/1994 | Goldberg et al. |
| 5,559,092 A | 9/1996 | Gibson et al. |
| 5,635,167 A * | 6/1997 | Said .................. A61K 8/44 424/701 |
| 5,804,172 A | 9/1998 | Ault |
| 5,847,003 A | 12/1998 | Ptchelintsev et al. |
| 6,069,169 A | 5/2000 | Ptchelintsev et al. |
| 6,071,962 A | 6/2000 | Ptchelintsev et al. |
| 6,287,547 B1 | 9/2001 | Oota et al. |
| 6,348,189 B1 | 2/2002 | Tanabe et al. |
| 6,358,502 B1 | 3/2002 | Tanabe et al. |
| 6,365,143 B1 | 4/2002 | Lundmark et al. |
| 6,380,263 B1 | 4/2002 | Pruche et al. |
| 6,432,147 B1 | 8/2002 | Dias et al. |
| 6,432,394 B2 | 8/2002 | Pyles et al. |
| 6,509,011 B1 | 1/2003 | Ellis et al. |
| 6,544,500 B1 | 4/2003 | O'Toole et al. |
| 6,551,361 B1 | 4/2003 | Cornwell et al. |
| 6,602,493 B2 | 8/2003 | Akhter et al. |
| 6,624,126 B1 | 9/2003 | Kasuga et al. |
| 6,743,434 B1 | 6/2004 | Lundmark et al. |
| 6,858,202 B2 | 2/2005 | Niemiec et al. |
| 6,864,314 B1 | 3/2005 | Yeung et al. |
| 6,927,196 B2 | 8/2005 | Snyder et al. |
| 7,045,493 B2 | 5/2006 | Wang et al. |
| 7,169,743 B2 | 1/2007 | Wang et al. |
| 7,186,274 B2 | 3/2007 | Vic et al. |
| 7,186,275 B2 | 3/2007 | Boswell |
| 7,300,647 B1 | 11/2007 | O'Toole et al. |
| 7,335,700 B2 | 2/2008 | Yeung et al. |

(Continued)

FOREIGN PATENT DOCUMENTS

| | | |
|---|---|---|
| CA | 1147262 A | 5/1983 |
| DE | 19536420 A1 | 4/1996 |

(Continued)

OTHER PUBLICATIONS

All Office Actions, U.S. Appl. No. 16/985,902.

(Continued)

*Primary Examiner* — David J Blanchard
*Assistant Examiner* — Sarah J Chickos
(74) *Attorney, Agent, or Firm* — John G. Powell

(57) ABSTRACT

A hair care composition that removes calcium fatty carboxylate salts from the hair and scalp is provided. The hair care composition includes a calcium chelant, an anionic surfactant, a hydrotrope, a carrier, and optionally a zwitterionic surfactant.

11 Claims, 4 Drawing Sheets

(56) References Cited

U.S. PATENT DOCUMENTS

| | | | |
|---|---|---|---|
| 7,547,454 | B2 | 6/2009 | Gupta |
| 7,700,078 | B2 | 4/2010 | Huglin et al. |
| 7,709,430 | B2 | 5/2010 | Mizushima |
| 7,745,382 | B2 | 6/2010 | Sloan |
| 7,915,212 | B2 | 3/2011 | Yeung et al. |
| 8,022,020 | B2 | 9/2011 | Sloan |
| 8,039,424 | B2 | 10/2011 | Sloan |
| 8,404,257 | B1 | 3/2013 | Huglin et al. |
| 8,449,868 | B2 | 5/2013 | Jennings et al. |
| 8,637,489 | B2 | 1/2014 | Van Nguyen et al. |
| 8,942,481 | B2 | 1/2015 | Suarez Cambre et al. |
| 9,044,413 | B2 | 6/2015 | Yeung et al. |
| 9,080,135 | B2 | 7/2015 | Hough et al. |
| 9,271,908 | B2 | 3/2016 | Allef et al. |
| 9,358,195 | B2 | 6/2016 | Lupia et al. |
| 9,586,063 | B2 | 3/2017 | Marsh et al. |
| 9,642,788 | B2 | 5/2017 | Marsh et al. |
| 10,539,872 | B2 | 1/2020 | Tadokoro |
| 2003/0095938 | A1 | 5/2003 | Casero |
| 2003/0125224 | A1* | 7/2003 | Seitz, Jr. .............. C11D 1/02 510/131 |
| 2003/0176303 | A1 | 9/2003 | Niemiec et al. |
| 2003/0211953 | A1 | 11/2003 | Glenn et al. |
| 2003/0215522 | A1 | 11/2003 | Johnson et al. |
| 2004/0058855 | A1 | 3/2004 | Schwartz et al. |
| 2004/0123402 | A1 | 7/2004 | Marsh et al. |
| 2004/0261198 | A1 | 12/2004 | Kainz et al. |
| 2004/0266656 | A1 | 12/2004 | Sakurai |
| 2005/0095215 | A1 | 5/2005 | Popp |
| 2005/0095261 | A1 | 5/2005 | Popp |
| 2005/0239723 | A1 | 10/2005 | Amin |
| 2005/0256313 | A1 | 11/2005 | Norenberg et al. |
| 2006/0009371 | A1 | 1/2006 | Wang et al. |
| 2006/0063695 | A1 | 3/2006 | Wang et al. |
| 2006/0130246 | A1 | 6/2006 | Molenda et al. |
| 2006/0287219 | A1 | 12/2006 | Dykstra |
| 2008/0005715 | A1 | 1/2008 | Shimizu et al. |
| 2008/0057015 | A1 | 3/2008 | Oblong et al. |
| 2008/0145328 | A1* | 6/2008 | Schwartz ............ A01N 59/16 424/70.11 |
| 2009/0071493 | A1 | 3/2009 | Nguyen et al. |
| 2009/0074700 | A1 | 3/2009 | Nguyen et al. |
| 2009/0092561 | A1 | 4/2009 | Lupia et al. |
| 2009/0119852 | A1* | 5/2009 | Marsh ................. A61K 8/411 8/408 |
| 2010/0069338 | A1 | 3/2010 | Ward et al. |
| 2010/0195039 | A1 | 8/2010 | Park |
| 2011/0015120 | A1 | 1/2011 | Bortolin |
| 2012/0034181 | A1 | 2/2012 | Hoffmann et al. |
| 2012/0034182 | A1 | 2/2012 | Hoffmann et al. |
| 2013/0122070 | A1 | 5/2013 | Barnett |
| 2013/0174863 | A1 | 7/2013 | Marsh et al. |
| 2013/0333715 | A1 | 12/2013 | Hutton, III et al. |
| 2014/0079660 | A1* | 3/2014 | Doi ..................... A61Q 5/02 424/70.24 |
| 2014/0213499 | A1 | 7/2014 | Chen et al. |
| 2014/0349902 | A1 | 11/2014 | Allef et al. |
| 2015/0011449 | A1* | 1/2015 | Snyder ................ A61K 8/894 510/122 |
| 2015/0030644 | A1 | 1/2015 | Oh et al. |
| 2015/0093420 | A1 | 4/2015 | Snyder et al. |
| 2015/0140052 | A1 | 5/2015 | Gizaw |
| 2015/0182431 | A1 | 7/2015 | Chaudhuri |
| 2016/0175210 | A1 | 6/2016 | Marsh et al. |
| 2018/0000705 | A1 | 1/2018 | Marsh |
| 2018/0000706 | A1 | 1/2018 | Marsh |
| 2018/0000713 | A1 | 1/2018 | Marsh |
| 2018/0000714 | A1 | 1/2018 | Marsh |
| 2018/0000715 | A1 | 1/2018 | Marsh et al. |
| 2019/0336426 | A1 | 11/2019 | Marsh |
| 2020/0360254 | A1 | 11/2020 | Marsh |

FOREIGN PATENT DOCUMENTS

| | | |
|---|---|---|
| DE | 10259199 A1 | 6/2004 |
| DE | 102011079664 A1 | 4/2012 |
| EP | 1046390 A1 | 10/2000 |
| EP | 1714634 A1 | 10/2006 |
| EP | 2067467 A2 | 6/2009 |
| FR | 2853529 A1 | 10/2004 |
| FR | 2853530 A1 | 10/2004 |
| FR | 2853531 A1 | 10/2004 |
| GB | 2288812 A | 1/1995 |
| GB | 2315770 A | 2/1998 |
| JP | S57109711 A | 7/1982 |
| JP | S63150213 A | 6/1988 |
| JP | 05262623 | 10/1993 |
| JP | 06041579 | 2/1994 |
| JP | H07258698 A | 10/1995 |
| JP | H09183996 A | 7/1997 |
| JP | H09291024 A | 11/1997 |
| JP | H11139941 A | 5/1999 |
| JP | 11180836 A | 7/1999 |
| JP | 11269487 | 10/1999 |
| JP | 2004059540 | 2/2004 |
| JP | 2006160708 A | 6/2006 |
| JP | 2008169183 | 7/2008 |
| JP | 2011046652 | 3/2011 |
| KR | 1020090077562 A | 7/2009 |
| WO | WO9116878 A1 | 11/1991 |
| WO | WO9311737 A1 | 6/1993 |
| WO | WO9804237 A1 | 2/1998 |
| WO | WO9824400 A2 | 6/1998 |
| WO | WO0051555 A1 | 9/2000 |
| WO | WO0051556 A1 | 9/2000 |
| WO | WO200119327 A1 | 3/2001 |
| WO | WO0220486 A2 | 3/2002 |
| WO | WO02065982 A2 | 8/2002 |
| WO | WO02102302 A2 | 12/2002 |
| WO | WO2007079793 A1 | 7/2007 |
| WO | WO2008136000 A2 | 11/2008 |
| WO | WO2008153050 A1 | 12/2008 |
| WO | WO2010106342 A2 | 9/2010 |
| WO | WO201220226 A1 | 2/2012 |
| WO | WO2012021472 A1 | 2/2012 |
| WO | WO2014182766 A1 | 11/2014 |

OTHER PUBLICATIONS

Charles N Reilley et al: "Chelan Approach to Analysis (I) Survey of Theory and Application", Journal of Chemical Education, Nov. 1, 1959 (Nov. 1, 1959 ), XP0557 40258,Retrieved from the Internet:URL:https://pubs.acs.org/doi/pdf/10.1021 /ed036p555?rand=jisnuiqf [retrieved on Oct. 15, 2020], pp. 555-564.
Alberto Culver, Canada, Shampoo, Mintel GNPD, Mar. 2008.
All final and non-final office actions for U.S. Appl. No. 13/737,035.
All final and non-final office actions for U.S. Appl. No. 13/920,171.
All final and non-final office actions for U.S. Appl. No. 15/630,411.
All final and non-final office actions for U.S. Appl. No. 15/630,426.
All final and non-final office actions for U.S. Appl. No. 15/630,431.
All final and non-final office actions for U.S. Appl. No. 15/630,437.
All final and non-final office actions for U.S. Appl. No. 15/630,899.
All final and non-final office actions for U.S. Appl. No. 16/515,821.
Gary W. Evans, "The Role of Picolinic acid in Metal Metabolism", Life Chemistry Reports, Jan. 1, 1982, pp. 57-67.
PCT International Search Report and Written Opinion for PCT/US2013/020735 dated Aug. 5, 2013.
PCT International Search Report and Written Opinion for PCT/US2017/038897 dated Sep. 18, 2017.
PCT International Search Report and Written Opinion for PCT/US2017/038899 dated Aug. 21, 2017.
PCT International Search Report and Written Opinion for PCT/US2017/038900 dated Aug. 21, 2017.
PCT International Search Report and Written Opinion for PCT/US2017/038903 dated Sep. 25, 2017.
PCT International Search Report and Written Opinion for PCT/US2017/038904 dated Sep. 18, 2017.

(56) References Cited

OTHER PUBLICATIONS

Procter & Gamble, UK, 0% Grease Shampoo, Mintel, Feb. 2016.
Vitality Unlimited: "What's A Picolinate?—Picolinic acid is the body's prime natural chelator", Dec. 30, 1989.
Zurowska Bogum Ed—Lippert Bernhard et al, "Structural and Magnetic characterization of Cu-picolinate and Cu-Quinaldinate nad their mixed complexes with water or halides", Inorganica Chimica Acta, vol. 418, May 2, 2014, pp. 136-152.

* cited by examiner

HAIR CARE COMPOSITIONS FOR CALCIUM CHELATION

FIELD OF THE INVENTION

Described herein is a hair care composition for removing calcium fatty carboxylate salts from the hair and scalp. The hair care composition comprises a calcium chelant, an anionic surfactant, a hydrotrope, and a carrier, wherein the hair care composition has a pH from about 4 to about 7. Methods of using the hair care compositions are also described herein.

BACKGROUND OF THE INVENTION

Many water sources that are used by consumers for personal care contain elevated levels of calcium ions. The calcium ions can react or combine with fatty acid molecules present on the hair or scalp. These fatty acid molecules may be from internal lipids or from sebum lipids. Upon combination of the calcium ions with the fatty acid molecules, calcium fatty carboxylate salts can be formed. Calcium fatty carboxylate salts are highly insoluble and can either be deposited onto the hair and scalp or they can precipitate inside the hair fiber, which can be detrimental to hair health and appearance. Hair with deposits of calcium fatty carboxylate salts can show reduced shine, are difficult to comb, and the deposits can eventually lead to fiber damage including cuticle breakage. Many current hair care compositions are not able to efficiently remove these calcium fatty carboxylate salts.

Thus, a hair care composition which could remove these calcium fatty carboxylate salts from the scalp and/or hair could lead to improved shine and compatibility, as well as reduced hair damage. Accordingly, there is a need for an improved hair care composition for removing calcium fatty carboxylate salts from the scalp and/or hair.

SUMMARY OF THE INVENTION

Described herein is a hair care composition comprising (a) from about 0.2% to about 10% of a calcium chelant by weight of the hair care composition, wherein the calcium chelant is selected from the group consisting of diethylenetriaminepentaacetic acid (DTPA), hydroxyethyl ethylenediamine triacetic acid (HEDTA), N-(2-acetamido)iminodiacetic acid (ADA), N-(2-hydroxyethyl)iminodiacetic acid (HIDA), etidronic acid (HEDP), pyrophosphoric acid, neridronic acid, aledronic acid, 2-pyridinol-1-oxide (HPNO), hinokitiol, and mixtures thereof; (b) from about 5% to about 40% of an anionic surfactant by weight of the hair care composition; (c) from about 0.2% to about 5% of a hydrotrope by weight of the hair care composition; and (d) from about 45% to about 95% of a carrier by weight of the hair care composition, wherein the pH of the hair care composition is from about 4 to about 7.

Also described herein is a method for removing deposits of calcium fatty carboxylate salts from hair comprising (a) applying a hair care composition to the hair comprising (i) from about 0.2% to about 10% of a calcium chelant by weight of the hair care composition, wherein the calcium chelant is selected from the group consisting of diethylenetriaminepentaacetic acid (DTPA), hydroxyethyl ethylenediamine triacetic acid (HEDTA), N-(2-acetamido)iminodiacetic acid (ADA), N-(2-hydroxyethyl)iminodiacetic acid (HIDA), etidronic acid (HEDP), pyrophosphoric acid, neridronic acid, aledronic acid, 2-pyridinol-1-oxide (HPNO), hinokitiol, and mixtures thereof; (ii) from about 5% to about 40% of an anionic surfactant by weight of the hair care composition; (iii) from about 0.2% to about 5% of a hydrotrope by weight of the hair care composition; and (iv) from about 45% to about 95% of a carrier by weight of the hair care composition, wherein the pH of the hair care composition is from about 4 to about 7; and (b) rinsing the hair care composition from the hair.

Also described herein is a hair care composition comprising (a) from about 0.5% to about 2% of a calcium chelant by weight of the hair care composition, wherein the calcium chelant is selected from the group consisting of diethylenetriaminepentaacetic acid (DTPA), hydroxyethyl ethylenediamine triacetic acid (HEDTA), N-(2-acetamido)iminodiacetic acid (ADA), N-(2-hydroxyethyl)iminodiacetic acid (HIDA), etidronic acid (HEDP), pyrophosphoric acid, neridronic acid, aledronic acid, 2-pyridinol-1-oxide (HPNO), hinokitiol, and mixtures thereof; (b) from about 5% to about 20% of an anionic surfactant by weight of the hair care composition; (c) from about 0.2% to about 3% of sodium xylenesulfonate by weight of the hair care composition; (d) from about 0.75% to about 2% of a zwitterionic surfactant by weight of the hair care composition; and (e) from about 45% to about 95% of a carrier by weight of the hair care composition, wherein the pH of the hair care composition is from about 4 to about 7.

DETAILED DESCRIPTION OF THE INVENTION

Figure 1:
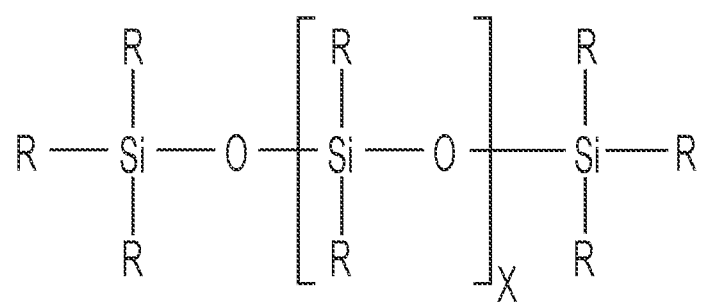
FIG. 1 illustrates formula VI, which is a chemical structure for a polyalkyl or polyaryl siloxane.

While the specification concludes with claims particularly pointing out and distinctly claiming the invention, it is believed that the disclosed subject matter will be better understood from the following description.

As used herein, the term "fluid" includes liquids and gels.

As used herein, the articles including "a" and "an" when used in a claim, are understood to mean one or more of what is claimed or described.

As used herein, "comprising" means that other steps and other ingredients which do not affect the end result can be added. This term encompasses the terms "consisting of" and "consisting essentially of".

As used herein, "mixtures" is meant to include a simple combination of materials and any compounds that may result from their combination.

As used herein, "molecular weight" or "Molecular weight" refers to the weight average molecular weight unless otherwise stated. Molecular weight of polymers may be measured using industry standard method, gel permeation chromatography ("GPC").

As used herein, "wt %," "weight %," "percent weight," or "by weight of the hair care composition" are meant to refer to the proportion of a component of the composition relative to the total weight of the hair care composition. Thus, if 2 wt % of component A is present in composition B, component A would be present at 2 g while the remaining components of composition B have a weight or mass of 98 g.

As used herein, the terms "include," "includes," and "including," are meant to be non-limiting and are understood to mean "comprise," "comprises," and "comprising," respectively.

All percentages, parts and ratios are based upon the total weight of the hair care composition, unless otherwise specified. All such weights as they pertain to listed ingredients are based on the active level and, therefore, do not include carriers or by-products that may be included in commercially available materials.

Unless otherwise noted, all component or composition levels are in reference to the active portion of that component or composition, and are exclusive of impurities, for example, residual solvents or by-products, which may be present in commercially available sources of such components or compositions.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

A. Calcium Chelants

Many consumers rely on water sources that contain elevated levels of calcium ions for washing their hair. These calcium ions can react with fatty acid compounds present on the hair and scalp to generate calcium fatty carboxylate salts. The fatty acid compounds found on the hair and scalp can be fully saturated or partially unsaturated. Saturated fatty acid compounds found on the hair and scalp can include caprylic acid, capric acid, lauric acid, myristic acid, palmitic acid, stearic acid, arachidic acid, behenic acid, lignoceric acid, and cerotic acid. Saturated fatty acid compounds found on the hair and scalp can be taken from the formula $CH_3(CH_2)_m COOH$, wherein m is equal to between 8 and 26.

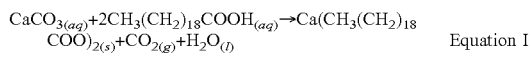

$$CaCO_{3(aq)} + 2CH_3(CH_2)_{18}COOH_{(aq)} \rightarrow Ca(CH_3(CH_2)_{18}COO)_{2(s)} + CO_{2(g)} + H_2O_{(l)} \quad \text{Equation I}$$

Calcium ions can be present in water systems as calcium carbonate, or $CaCO_3$, which can react with fatty acid compounds to generate calcium fatty carboxylate salts, as in Equation I. A calcium chelation composition that is not designed to chelate the calcium ion while solubilizing the fatty chain from the fatty carboxylate anion may not be able to remove the deposits of calcium fatty carboxylate salts. For example, calcium stearate, a calcium fatty carboxylate salt that can be found in hair, has a water solubility of 0.0004 g/100 mL of water. Thus, it can be difficult to remove calcium stearate without a particularly formulated composition.

The hair care composition described herein comprises from about 0.2% to about 10%, alternatively from about 0.2% to about 5%, alternatively from about 0.5% to about 5%, alternatively from about 0.5% to about 1.5%, and alternatively from about 1% to about 2% of one or more calcium chelants, by weight of the hair care composition.

In an embodiment, the calcium chelant can be selected from the group consisting of diethylenetriaminepentaacetic acid (DTPA), hydroxyethyl ethylenediamine triacetic acid (HEDTA), methylglycinediacetic acid (MGDA), ethylenediaminetetraacetic acid (EDTA), N-(2-acetamido)iminodiacetic acid (ADA), N-(2-hydroxyethyl)iminodiacetic acid (HIDA), etidronic acid (HEDP), pyrophosphoric acid, neridronic acid, aledronic acid, diethylenetriamine penta (methylene phosphonic acid) (DTPMP), 2-pyridinol-1-oxide (HPNO) hinokitiol, octopirox, and mixtures thereof.

In an embodiment, the calcium chelant can be selected from the group consisting of diethylenetriaminepentaacetic acid (DTPA), hydroxyethyl ethylenediamine triacetic acid (HEDTA), methylglycinediacetic acid (MGDA), ethylenediaminetetraacetic acid (EDTA), N-(2-acetamido)iminodiacetic acid (ADA), N-(2-hydroxyethyl)iminodiacetic acid (HIDA), sodium cocoamphoacetate (CADA), sodium lauroamphoacetate (NaLAA), iminodiacetic acid (IDA), N,N-diacetic acid (GLDA), ethylenediamine-N,N'-disuccinic acid (EDDS), histidine, glycine, etidronic acid (HEDP), pyrophosphoric acid, neridronic acid, aledronic acid, diethylenetriamine penta(methylene phosphonic acid) (DTPMP), phytic acid, di-(2-ethylhexyl)phosphoric acid (D2HEPA), 2-pyridinol-1-oxide (HPNO) hinokitiol, octopirox, pyrithione, picolinic acid, deferiprone and mixtures thereof.

In an embodiment, the calcium chelant can be selected from the group consisting of diethylenetriaminepentaacetic acid (DTPA), hydroxyethyl ethylenediamine triacetic acid (HEDTA), N-(2-acetamido)iminodiacetic acid (ADA), N-(2-hydroxyethyl)iminodiacetic acid (HIDA), etidronic acid (HEDP), pyrophosphoric acid, neridronic acid, aledronic acid, 2-pyridinol-1-oxide (HPNO), hinokitiol, and mixtures thereof.

In an embodiment, the calcium chelant can be represented by Formula I:

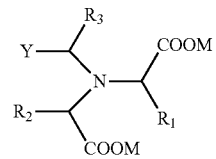

wherein $R_1$, $R_2$, and $R_3$ are independently selected from hydrogen, methyl, or ethyl;

wherein Y is —COOM, —CH$_2$OH, or —CONH$_2$; and wherein M is hydrogen or a alkaline metal cation.

In an embodiment, the calcium chelant can be represented by Formula II:

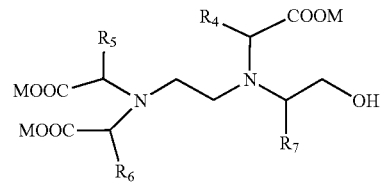

wherein $R_4$, $R_5$, $R_6$, and $R_7$ are independently selected from hydrogen, methyl, or ethyl; and wherein M is hydrogen or a alkaline metal cation.

In an embodiment, the calcium chelant can be represented by Formula III:

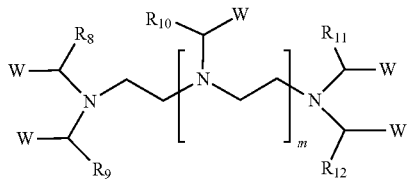

wherein $R_8$, $R_9$, $R_{10}$, $R_{11}$, and $R_{12}$ are independently selected from hydrogen, methyl, or ethyl; and
wherein W is —COOM, or —$PO_3M_1M_2$;
wherein M, $M_1$, and $M_2$ are independently selected from hydrogen or an alkaline metal cation;
and wherein m is 0, 1, 2, or 3.

In an embodiment, the calcium chelant can be represented by Formula IV:

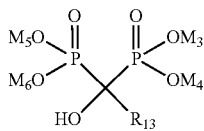

wherein $R_{13}$ is selected from methyl, ethyl, propyl, or —$CH_2(CH_2)_n$—$NH_2$,
wherein n is 0, 1, 2, 3, 4, 5, 6, or 7;
wherein $M_3$, $M_4$, $M_5$, and $M_6$ are independently selected from hydrogen or an alkaline metal cation.

In an embodiment, the calcium chelant can be represented by Formula V.

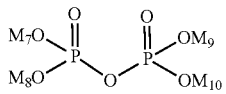

wherein $M_7$, $M_8$, $M_9$, and Mio are independently selected from hydrogen or an alkaline metal cation.

In an embodiment, the calcium chelant can be selected from the group consisting of a compound from Formula I, a compound from Formula II, a compound from Formula III, a compound from Formula IV, a compound from Formula V, 2-pyridinol-1-oxide (HPNO), hinokitiol, octopirox, and mixtures thereof.

B. Anionic Surfactant

The hair care composition may comprise from about 5% to about 40%, alternatively from about 5% to about 20%, or alternatively from about 10% to about 15% of one or more anionic surfactants, by weight of the hair care composition.

In an embodiment, anionic surfactants which may be suitable for use in the hair care composition are the alkyl and alkyl ether sulfates. Other suitable anionic surfactants may include the water soluble salts of organic, sulfuric acid reaction products. Still other suitable anionic surfactants may include the reaction products of fatty acids esterified with isethionic acid and neutralized with sodium hydroxide. Exemplary anionic surfactants for use in the hair care composition include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium cocoyl isethionate and combinations thereof. In a further embodiment, the anionic surfactant is sodium lauryl sulfate or sodium laureth sulfate.

In an embodiment, the hair care compositions can comprise ammonium C10-15 pareth sulfate, ammonium C10-15 alkyl sulfate, ammonium C11-15 alkyl sulfate, ammonium decyl sulfate, ammonium deceth sulfate, ammonium undecyl sulfate, ammonium undeceth sulfate, sodium C10-15 pareth sulfate, sodium C10-15 alkyl sulfate, sodium C11-15 alkyl sulfate, sodium decyl sulfate, sodium deceth sulfate, sodium undecyl sulfate, sodium undeceth sulfate, potassium C10-15 pareth sulfate, potassium C10-15 alkyl sulfate, potassium C11-15 alkyl sulfate, potassium decyl sulfate, potassium deceth sulfate, potassium undecyl sulfate, and/or potassium undeceth sulfate.

In an embodiment, suitable anionic surfactants include, but are not limited to undecyl sulfate compound selected from the group consisting of:
a) $R_1O(CH_2CHR_3O)_y$ $SO_3M$;
b) $CH_3(CH_2)_zCHR_2CH_2O(CH_2CHR_3O)_ySO_3M$; and
c) mixtures thereof, where $R_1$ represents $CH_3(CH_2)_{10}$, $R_2$ represents H or a hydrocarbon radical comprising 1 to 4 carbon atoms such that the sum of the carbon atoms in z and $R_2$ is 8, $R_3$ is H or $CH_3$, y is 0 to 7, the average value of y is about 1 when y is not zero (0), and M is a monovalent or divalent, positively-charged cation.

In an embodiment, suitable anionic alkyl sulfates and alkyl ether sulfate surfactants include, but are not limited to, those having branched alkyl chains which are synthesized from C8 to C18 branched alcohols which may be selected from the group consisting of: Guerbet alcohols, aldol condensation derived alcohols, oxo alcohols and mixtures thereof. Non-limiting examples of the 2-alkyl branched alcohols include oxo alcohols such as 2-methyl-1-undecanol, 2-ethyl-1-decanol, 2-propyl-1-nonanol, 2-butyl 1-octanol, 2-methyl-1-dodecanol, 2-ethyl-1-undecanol, 2-propyl-1-decanol, 2-butyl-1-nonanol, 2-pentyl-1-octanol, 2-pentyl-1-heptanol, and those sold under the tradenames LIAL® (Sasol), ISALCHEM® (Sasol), and NEODOL® (Shell), and Guerbet and aldol condensation derived alcohols such as 2-ethyl-1-hexanol, 2-propyl-1-butanol, 2-butyl-1-octanol, 2-butyl-1-decanol, 2-pentyl-1-nonanol, 2-hexyl-1-octanol, 2-hexyl-1-decanol and those sold under the tradename ISOFOL® (Sasol) or sold as alcohol ethoxylates and alkoxylates under the tradenames LUTENSOL XP® (BASF) and LUTENSOL XL® (BASF).

In an embodiment, the anionic alkyl sulfates and alkyl ether sulfates may also include those synthesized from C8 to C18 branched alcohols derived from butylene or propylene which are sold under the trade names EXXAL™ (Exxon) and Marlipal® (Sasol). This includes anionic surfactants of the subclass of sodium trideceth-n sulfates (STnS), where n is between about 0.5 and about 3.5. Exemplary surfactants of this subclass are sodium trideceth-2 sulfates and sodium trideceth-3 sulfates. The hair care composition can also include sodium tridecyl sulfate.

In an embodiment, the anionic surfactant can be used to solubilize or form a micelle around the fatty acid compound and/or the fatty carboxylate anion. In an embodiment, the anionic surfactant can be selected to correspond to the chain length of the fatty carboxylate anion and/or fatty acid compound.

C. Zwitterionic Surfactant

The hair care composition can comprise a zwitterionic surfactant for enhancing the chelation ability of the calcium chelant.

The hair care composition may comprise from about 0.25% to about 14%, alternatively from about 1% to about 12%, alternatively from about 3% to about 10%, alternatively from about 0.5% to about 5%, alternatively from about 0.75% to about 2% of one or more zwitterionic surfactants, by weight of the hair care composition. The zwitterionic surfactant can include, but is not limited to, lauramidopropyl betaine, cocoamidopropyl betaine, lauryl hydroxysultaine, sodium lauroamphoacetate, coco monoethanolamide and mixtures thereof.

Suitable zwitterionic surfactants for use in the hair care composition described herein include those which are known for use in shampoo or other hair care cleansing.

The hair care composition may comprises a zwitterionic surfactant, wherein the zwitterionic surfactant is a derivative of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group such as carboxy, sulfonate, sulfate, phosphate or phosphonate. The zwitterionic surfactant can be selected from the group consisting of: cocamidoethyl betaine, cocamidopropylamine oxide, cocamidopropyl betaine, cocamidopropyl dimethylaminohydroxypropyl hydrolyzed collagen, cocamidopropyldimonium hydroxypropyl hydrolyzed collagen, cocamidopropyl hydroxysultaine, cocobetaineamido amphopropionate, coco-betaine, coco-hydroxysultaine, coco/oleamidopropyl betaine, coco-sultaine, lauramidopropyl betaine, lauryl betaine, lauryl hydroxysultaine, lauryl sultaine, and mixtures thereof. A suitable zwitterionic surfactant is lauryl hydroxysultaine.

In an embodiment, the zwitterionic surfactant can be selected from the group consisting of lauryl hydroxysultaine, cocamidopropyl hydroxysultaine, coco-betaine, cocohydroxysultaine, coco-sultaine, lauryl betaine, lauryl sultaine, and mixtures thereof.

D. Hydrotrope

The hair care composition may comprise from about 0.1% to about 5%, alternatively from about 0.2% to about 3%, or alternatively from about 0.3% to about 3% of one or more hydrotropes by weight of the hair care composition.

In an embodiment, the hydrotrope can solubilize a fatty or hydrophobic compound in an aqueous solution. In an embodiment, the hydrotrope can have a hydrophobic portion and a hydrophilic portion.

In an embodiment, the hydrotrope can be selected from the group consisting of salts of xylene sulfonic acid, toluene sulfonic acid, cumene sulfonic acid, and mixtures thereof.

E. Carrier

The hair care compositions can be in the form of pourable liquids (under ambient conditions). Such hair care compositions will therefore typically comprise a carrier, which is present at a level of from about 20% to about 95%, from about 45% to about 95%, or even from about 60% to about 85%, by weight of the hair care composition. The carrier may comprise water, an organic solvent, and mixtures thereof. In an embodiment, the carrier may comprise water with minimal or no significant concentrations of organic solvent, except as otherwise incidentally incorporated into the hair care composition as minor ingredients of other essential or optional components.

The carrier can include water and water solutions of lower alkyl alcohols and polyhydric alcohols. The lower alkyl alcohols useful herein are monohydric alcohols having 1 to 6 carbons, in one aspect, ethanol and isopropanol. Exemplary polyhydric alcohols useful herein include propylene glycol, hexylene glycol, glycerin, and propane diol.

In an embodiment, the pH of the hair care composition is from about 4 to about 7. In an embodiment, the pH of the hair care composition is from about 5 to about 7. In an embodiment, the pH of the hair care composition is from about 6 to about 7. In an embodiment, the pH of the hair care composition is from about 4 to about 6. In an embodiment the pH of the hair care composition is from about 5 to about 6. The pH can be modified and controlled by using a buffer system. In one aspect of the buffering system, the organic acid is selected from an alpha-hydroxy acid, a polycarboxylic acid, or mixtures thereof. Accordingly, the organic acid has an acidic functional group having a pKa of about 4.5 or less. In another embodiment, the organic has a second acidic functional group having a pKa of about 6 or less. The organic acids having multiple acidic functional groups can provide improved buffering capacity relative to their single acidic functional group counterparts. In one aspect, the organic acid may have a molecular weight less than about 500 grams per mole (g/mol) to afford enhanced molar efficiency. For example, the molecular weight of the organic acid may be from about 90 g/mol to about 400 g/mol, from about 100 g/mol to about 300 g/mol, from about 130 g/mol to about 250 g/mol, from about 150 g/mol to about 200, or about 190 g/mole. In another aspect, the organic acid may be soluble in water in an amount greater than about 0.2 moles per liter at 25° C. For example, the water solubility of the organic acid may be about 0.3 mol/L or more, about 0.4 mol/L or more, or about 0.5 mol/L or more.

In an embodiment, the organic acid is selected from an alpha-hydroxy acid, a polycarboxylic acid, or mixtures thereof. In an embodiment, the alpha-hydroxy acid is selected from citric acid, malic acid, tartaric acid, or combinations thereof. In an embodiment, the polycarboxylic acid is malonic acid. In an embodiment, the organic acid is citric acid. Further, examples of the salt of such an organic acid can include its alkali metal salts such as the sodium salt and the potassium salt; its ammonium salt; and its alkanolamine salts such as the triethanolamine salt.

No particular limitation is imposed on the amount of the pH buffering agent to be added, and its amount varies depending on the nature of the compound giving buffering ability. When sodium citrate is used as a primary compound giving the buffering ability, for example, it can be added at a concentration of about 0.5 wt % to about 8 wt %, about 1 wt % to about 5 wt %, about 1 wt % to about 4 wt %, or about 2 wt % to about 3 wt % to provide the desired level of buffering capacity.

F. Gel Network

In an embodiment, the hair care composition may also comprise fatty alcohol gel networks, which have been used for years in cosmetic creams and hair conditioners. These gel networks are formed by combining fatty alcohols and surfactants in the ratio of 1:1 to 40:1, alternatively from 2:1 to 20:1, and alternatively from 3:1 to 10:1. The formation of a gel network involves heating a dispersion of the fatty alcohol in water with the surfactant to a temperature above the melting point of the fatty alcohol. During the mixing process, the fatty alcohol melts, allowing the surfactant to partition into the fatty alcohol droplets. The surfactant brings water along with it into the fatty alcohol. This changes the isotropic fatty alcohol drops into liquid crystalline phase drops. When the mixture is cooled below the chain melt temperature, the liquid crystal phase is converted into a solid crystalline gel network. The gel network contributes a stabilizing benefit to cosmetic creams and hair conditioners. In addition, they deliver conditioned feel benefits for hair conditioners.

Thus according to an embodiment, the fatty alcohol is included in the fatty alcohol gel network at a level by weight of from about 0.05 wt % to about 14 wt %. For example, the fatty alcohol may be present in an amount ranging from about 1 wt % to about 10 wt %, and in another embodiment from about 6 wt % to about 8 wt %.

The fatty alcohols useful herein are those having from about 10 to about 40 carbon atoms, from about 12 to about 22 carbon atoms, from about 16 to about 22 carbon atoms, or about 16 to about 18 carbon atoms. These fatty alcohols can be straight or branched chain alcohols and can be saturated or unsaturated. Nonlimiting examples of fatty alcohols include, cetyl alcohol, stearyl alcohol, behenyl alcohol, and mixtures thereof. Mixtures of cetyl and stearyl alcohol in a ratio of from about 20:80 to about 80:20 are suitable.

Gel network preparation: A vessel is charged with water and the water is heated to about 74° C. Cetyl alcohol, stearyl alcohol, and SLES surfactant are added to the heated water. After incorporation, the resulting mixture is passed through a heat exchanger where the mixture is cooled to about 35° C. Upon cooling, the fatty alcohols and surfactant crystallized to form a crystalline gel network. Table 1 provides the components and their respective amounts for the gel network composition.

TABLE 1

Gel network components

| Ingredient | Wt. % |
| --- | --- |
| Water | 78.27% |
| Cetyl Alcohol | 4.18% |
| Steary Alcohol | 7.52% |
| Sodium laureth-3 sulfate (28% Active) | 10.00% |
| 5-Chloro-2-methyl-4-isothiazolin-3-one, Kathon CG | 0.03% |

G. Optional Ingredients

The hair care composition described herein may further comprise one or more additional components known for use in hair care or personal care products, provided that the additional components are physically and chemically compatible with the essential components described herein, or do not otherwise unduly impair product stability, aesthetics or performance. Such optional ingredients are most typically those described in reference books such as the CTFA Cosmetic Ingredient Handbook, Second Edition, The Cosmetic, Toiletries, and Fragrance Association, Inc. 1988, 1992. Individual concentrations of such additional components may range from about 0.001 wt % to about 10 wt % by weight of the hair care compositions.

Non-limiting examples of additional components for use in the hair care composition include conditioning agents (e.g., silicones, hydrocarbon oils, fatty esters), natural cationic deposition polymers, synthetic cationic deposition polymers, anti-dandruff agents, particles, suspending agents, paraffinic hydrocarbons, propellants, viscosity modifiers, dyes, non-volatile solvents or diluents (water-soluble and water-insoluble), pearlescent aids, foam boosters, additional surfactants or nonionic cosurfactants, pediculocides, pH adjusting agents, perfumes, preservatives, proteins, skin active agents, sunscreens, UV absorbers, and vitamins.

1. Conditioning Agent

In an embodiment, the hair care compositions comprise one or more conditioning agents. Conditioning agents include materials that are used to give a particular conditioning benefit to hair and/or skin. The conditioning agents useful in the hair care composition can comprise a water-insoluble, water-dispersible, non-volatile, liquid that forms emulsified, liquid particles. Suitable conditioning agents for use in the hair care composition are those conditioning agents characterized generally as silicones (e.g., silicone oils, cationic silicones, silicone gums, high refractive silicones, and silicone resins), organic conditioning oils (e.g., hydrocarbon oils, polyolefins, and fatty esters) or combinations thereof, or those conditioning agents which otherwise form liquid, dispersed particles in the aqueous surfactant matrix.

In an embodiment, one or more conditioning agents are present from about 0.01 wt % to about 10 wt %, from about 0.1 wt % to about 8 wt %, and from about 0.2 wt % to about 4 wt %, by weight of the hair care composition.

a. Silicones

The conditioning agent of the hair care composition can be an insoluble silicone conditioning agent. The silicone conditioning agent particles may comprise volatile silicone, non-volatile silicone, or combinations thereof. In one embodiment the conditioning agent is a non-volatile silicone conditioning agents. If volatile silicones are present, it will typically be incidental to their use as a solvent or carrier for commercially available forms of non-volatile silicone materials ingredients, such as silicone gums and resins. The silicone conditioning agent particles may comprise a silicone fluid conditioning agent and may also comprise other ingredients, such as a silicone resin to improve silicone fluid deposition efficiency or enhance glossiness of the hair.

The concentration of the silicone conditioning agent typically ranges from about 0.01% to about 10%, alternatively from about 0.1% to about 8%, alternatively from about 0.1% to about 5%, and alternatively from about 0.2% to about 3% by weight of the hair care composition. The silicone conditioning agents for use in the hair care composition can have a viscosity, as measured at 25Â° C., from about 20 to about 2,000,000 centistokes ("csk"), from about 1,000 to about 1,800,000 csk, from about 50,000 to about 1,500,000 csk, and from about 100,000 to about 1,500,000 csk.

The dispersed silicone conditioning agent particles typically have a volume average particle diameter ranging from about 0.01 micrometer to about 50 micrometer. For small particle application to hair, the volume average particle diameters typically range from about 0.01 micrometer to about 4 micrometer, from about 0.01 micrometer to about 2 micrometer, from about 0.01 micrometer to about 0.5 micrometer. For larger particle application to hair, the volume average particle diameters typically range from about 5 micrometer to about 125 micrometer, from about 10 micrometer to about 90 micrometer, from about 15 micrometer to about 70 micrometer, from about 20 micrometer to about 50 micrometer.

Background material on silicones including sections discussing silicone fluids, gums, and resins, as well as manufacture of silicones, are found in *Encyclopedia of Polymer Science and Engineering*, vol. 15, 2d ed., pp 204-308, John Wiley & Sons, Inc. (1989), incorporated herein by reference.

i. Silicone Oils

Silicone fluids include silicone oils, which are flowable silicone materials having a viscosity, as measured at 25° C., less than 1,000,000 csk, from about 5 csk to about 1,000,000 csk, from about 100 csk to about 600,000 csk. Suitable silicone oils for use in the hair care composition include polyalkyl siloxanes, polyaryl siloxanes, polyalkylaryl siloxanes, polyether siloxane copolymers, and mixtures thereof. Other insoluble, non-volatile silicone fluids having hair conditioning properties may also be used.

Silicone oils include polyalkyl or polyaryl siloxanes which conform to Formula (VI), which is shown in FIG. 1, wherein R is aliphatic, in one embodiment alkyl or alkenyl, or aryl, R can be substituted or unsubstituted, and x is an integer from 1 to about 8,000. Suitable R groups for use in the hair care composition include, but are not limited to: alkoxy, aryloxy, alkaryl, arylalkyl, arylalkenyl, alkamino, and ether-substituted, hydroxyl-substituted, and halogen-substituted aliphatic and aryl groups. Suitable R groups also include cationic amines and quaternary ammonium groups.

Suitable alkyl and alkenyl substituents are $C_1$ to $C_5$ alkyls and alkenyls, from $C_1$ to $C_4$, alternatively from $C_1$ to $C_2$. The aliphatic portions of other alkyl-, alkenyl-, or alkynyl-containing groups (such as alkoxy, alkaryl, and alkamino) can be straight or branched chains, and can be from $C_1$ to $C_5$, from $C_1$ to $C_4$, from $C_1$ to $C_3$, from $C_1$ to $C_2$. As discussed above, the R substituents can also contain amino functionalities (e.g. alkamino groups), which can be primary, secondary or tertiary amines or quaternary ammonium. These include mono-, di- and tri-alkylamino and alkoxyamino groups, wherein the aliphatic portion chain length can be as described herein.

ii. Amino and Cationic Silicones

Cationic silicone fluids suitable for use in the hair care composition include, but are not limited to, those which conform to the general formula (II):

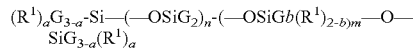

wherein G is hydrogen, phenyl, hydroxy, or $C_1$-$C_8$ alkyl, in one embodiment is methyl; a is 0 or an integer having a value from 1 to 3, in one embodiment 0; b is 0 or 1, in one embodiment 1; n is a number from 0 to 1,999, and in one embodiment from 49 to 499; m is an integer from 1 to 2,000, in one embodiment from 1 to 10; the sum of n and m is a number from 1 to 2,000, in one embodiment from 50 to 500; R' is a monovalent radical conforming to the general formula $CqH_{2q}L$, wherein q is an integer having a value from 2 to 8 and L is selected from the following groups:

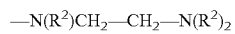

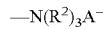

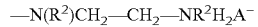

wherein $R^2$ is hydrogen, phenyl, benzyl, or a saturated hydrocarbon radical, in one embodiment an alkyl radical from about $C_1$ to about $C_{20}$, and $A^-$ is a halide ion.

Figure 2:
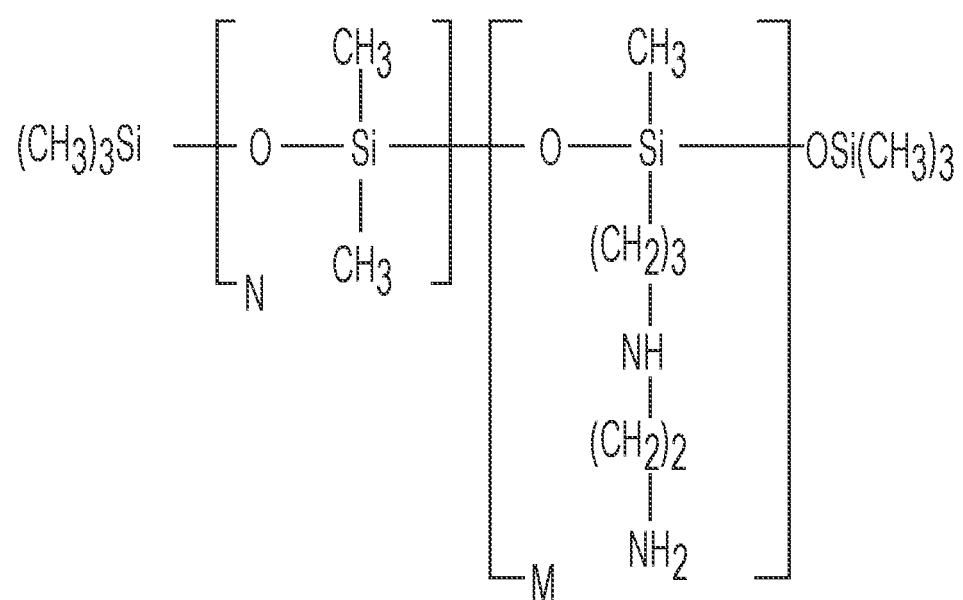
FIG. 2 illustrates formula VII, which is a chemical structure for trimethylsilylamodimethicone.
Figure 3:
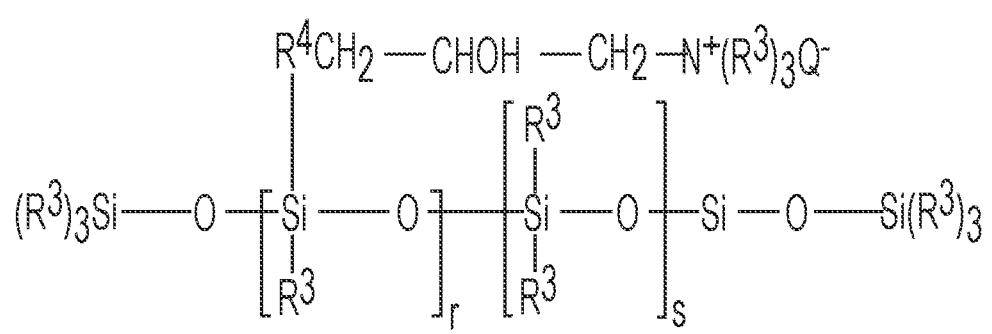
FIG. 3 illustrates formula VIII, which is a general chemical structure for a silicone cationic polymer.

In one embodiment the cationic silicone corresponding to formula (VI) is the polymer known as "trimethylsilylamodimethicone", which is shown in FIG. 2 as formula (VII). Other silicone cationic polymers which may be used in the hair care composition are represented by the general formula (VIII), which is shown in FIG. 3, wherein $R^3$ is a monovalent hydrocarbon radical from $C_1$ to $C_{18}$, in one embodiment an alkyl or alkenyl radical, such as methyl; $R_4$ is a hydrocarbon radical, in one embodiment a $C_1$ to $C_{18}$ alkylene radical or a $C_{10}$ to $C_{18}$ alkyleneoxy radical, in one embodiment a $C_1$ to $C_8$ alkyleneoxy radical; $Q^-$ is a halide ion, in one embodiment chloride; r is an average statistical value from 2 to 20, in one embodiment from 2 to 8; s is an average statistical value from 20 to 200, in one embodiment from 20 to 50. One suitable example of a polymer in this class is known as UCARE SILICONE ALE 56®, available from Union Carbide.

iii. Silicone Gums

Other silicone fluids suitable for use in the hair care composition are the insoluble silicone gums. These gums are polyorganosiloxane materials having a viscosity, as measured at 25° C., of greater than or equal to 1,000,000 csk. Silicone gums are described in U.S. Pat. No. 4,152,416; Noll and Walter, Chemistry and Technology of Silicones, New York: Academic Press (1968); and in General Electric Silicone Rubber Product Data Sheets SE 30, SE 33, SE 54 and SE 76, all of which are incorporated herein by reference. Specific non-limiting examples of silicone gums for use in the hair care composition include polydimethylsiloxane, (polydimethylsiloxane)(methylvinylsiloxane)copolymer, poly(dimethylsiloxane)(diphenyl siloxane)(methylvinylsiloxane)copolymer and mixtures thereof.

iv. High Refractive Index Silicones

Other non-volatile, insoluble silicone fluid conditioning agents that are suitable for use in the hair care composition are those known as "high refractive index silicones," having a refractive index of at least about 1.46, at least about 1.48, at least about 1.52, or at least about 1.55. The refractive index of the polysiloxane fluid will generally be less than about 1.70, typically less than about 1.60. In this context, polysiloxane "fluid" includes oils as well as gums.

Figure 4:
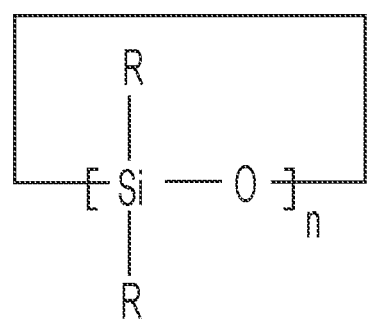
FIG. 4 illustrates formula IX, which is a chemical structure for a cyclic polysiloxane.

The high refractive index polysiloxane fluid includes those represented by general Formula (VI) above, as well as cyclic polysiloxanes such as those represented by Formula (IX) shown in FIG. 4, wherein R is as defined above, and n is a number from about 3 to about 7, or from about 3 to about 5.

The high refractive index polysiloxane fluids contain an amount of aryl-containing R substituents sufficient to increase the refractive index to the desired level, which is described herein. Additionally, R and n must be selected so that the material is non-volatile.

Aryl-containing substituents include those which contain alicyclic and heterocyclic five and six member aryl rings and those which contain fused five or six member rings. The aryl rings themselves can be substituted or unsubstituted.

Generally, the high refractive index polysiloxane fluids will have a degree of aryl-containing substituents of at least about 15%, at least about 20%, at least about 25%, at least about 35%, at least about 50%. Typically, the degree of aryl substitution will be less than about 90%, more generally less than about 85%, and in one embodiment from about 55% to about 80%. Suitable high refractive index polysiloxane fluids have a combination of phenyl or phenyl derivative substituents, with alkyl substituents, in one embodiment $C_1$-$C_4$ alkyl (in one embodiment methyl), hydroxy, or $C_1$-$C_4$ alkylamino (especially —R$^4$NHR$^5$NH2 wherein each R$^4$ and R$^5$ independently is a C$_1$-C$_3$ alkyl, alkenyl, and/or alkoxy).

When high refractive index silicones are used in the hair care composition, they can be used in solution with a spreading agent, such as a silicone resin or a surfactant, to reduce the surface tension by a sufficient amount to enhance spreading and thereby enhance the glossiness (subsequent to drying) of hair treated with the compositions.

Silicone fluids suitable for use in the hair care composition are disclosed in U.S. Pat. Nos. 2,826,551, 3,964,500, 4,364,837, British Pat. No. 849,433, and Silicon Compounds, Petrarch Systems, Inc. (1984), all of which are incorporated herein by reference.

v. Silicone Resins

Silicone resins may be included in the silicone conditioning agent of the hair care composition. These resins are highly cross-linked polymeric siloxane systems. The cross-linking is introduced through the incorporation of trifunctional and tetrafunctional silanes with monofunctional or difunctional, or both, silanes during manufacture of the silicone resin.

Silicone materials and silicone resins in particular, can conveniently be identified according to a shorthand nomenclature system known to those of ordinary skill in the art as "MDTQ" nomenclature. Under this system, the silicone is described according to presence of various siloxane monomer units which make up the silicone. Briefly, the symbol M denotes the monofunctional unit (CH$_3$)$_3$SiO$_{0.5}$; D denotes the difunctional unit (CH$_3$)$_2$SiO; T denotes the trifunctional unit (CH$_3$)SiO$_{1.5}$; and Q denotes the quadra- or tetra-functional unit SiO$_2$. Primes of the unit symbols (e.g. M', D', T', and Q') denote substituents other than methyl, and must be specifically defined for each occurrence.

Suitable silicone resins for use in the hair care composition include, but are not limited to MQ, MT, MTQ, MDT and MDTQ resins. Methyl is a suitable silicone substituent. Other suitable silicone resins include MQ resins, wherein the M:Q ratio is from about 0.5:1.0 to about 1.5:1.0 and the average molecular weight of the silicone resin is from about 1000 to about 10,000.

The weight ratio of the non-volatile silicone fluid, having refractive index below 1.46, to the silicone resin component, when used, can be from about 4:1 to about 400:1, from about 9:1 to about 200:1, from about 19:1 to about 100:1, particularly when the silicone fluid component is a polydimethylsiloxane fluid or a mixture of polydimethylsiloxane fluid and polydimethylsiloxane gum as described herein. Insofar as the silicone resin forms a part of the same phase in the compositions hereof as the silicone fluid, i.e. the conditioning active, the sum of the fluid and resin should be included in determining the level of silicone conditioning agent in the composition.

b. Organic Conditioning Oils

The conditioning agent of the hair care composition may also comprise at least one organic conditioning oil, either alone or in combination with other conditioning agents, such as the silicones described above.

i. Hydrocarbon Oils

Suitable organic conditioning oils for use as conditioning agents in the hair care composition include, but are not limited to, hydrocarbon oils having at least about 10 carbon atoms, such as cyclic hydrocarbons, straight chain aliphatic hydrocarbons (saturated or unsaturated), and branched chain aliphatic hydrocarbons (saturated or unsaturated), including polymers and mixtures thereof. Straight chain hydrocarbon oils can be from about C$_{12}$ to about C$_{19}$. Branched chain hydrocarbon oils, including hydrocarbon polymers, typically will contain more than 19 carbon atoms.

ii. Polyolefins

Organic conditioning oils for use in the hair care composition can also include liquid polyolefins, including liquid poly-α-olefins and/or hydrogenated liquid poly-α-olefins. Polyolefins for use herein are prepared by polymerization of C$_4$ to about C$_{14}$ olefinic monomers, and in one embodiment from about C$_6$ to about C$_{12}$.

iii. Fatty Esters

Other suitable organic conditioning oils for use as the conditioning agent in the hair care composition includes fatty esters having at least 10 carbon atoms. These fatty esters include esters with hydrocarbyl chains derived from fatty acids or alcohols. The hydrocarbyl radicals of the fatty esters hereof may include or have covalently bonded thereto other compatible functionalities, such as amides and alkoxy moieties (e.g., ethoxy or ether linkages, etc.).

iv. Fluorinated Conditioning Compounds

Fluorinated compounds suitable for delivering conditioning to hair or skin as organic conditioning oils include perfluoropolyethers, perfluorinated olefins, fluorine based specialty polymers that may be in a fluid or elastomer form similar to the silicone fluids previously described, and perfluorinated dimethicones.

v. Fatty Alcohols

Other suitable organic conditioning oils for use in the hair care composition can include, but are not limited to, fatty alcohols having at least about 10 carbon atoms, about 10 to about 22 carbon atoms, and in one embodiment about 12 to about 16 carbon atoms.

vi. Alkyl Glucosides and Alkyl Glucoside Derivatives

Suitable organic conditioning oils for use in the hair care composition include, but are not limited to, alkyl glucosides and alkyl glucoside derivatives. Specific non-limiting examples of suitable alkyl glucosides and alkyl glucoside derivatives include Glucam E-10, Glucam E-20, Glucam P-10, and Glucquat 125 commercially available from Amerchol.

c. Other Conditioning Agents i. Quaternary Ammonium Compounds

Suitable quaternary ammonium compounds for use as conditioning agents in the hair care composition can include, but are not limited to, hydrophilic quaternary ammonium compounds with a long chain substituent having a carbonyl moiety, like an amide moiety, or a phosphate ester moiety or a similar hydrophilic moiety.

Examples of useful hydrophilic quaternary ammonium compounds include, but are not limited to, compounds designated in the CTFA Cosmetic Dictionary as ricinoleamidopropyl trimonium chloride, ricinoleamido trimonium ethylsulfate, hydroxy stearamidopropyl trimoniummethylsulfate and hydroxy stearamidopropyl trimonium chloride, or combinations thereof.

ii. Polyethylene Glycols

Additional compounds useful herein as conditioning agents include polyethylene glycols and polypropylene glycols having a molecular weight of up to about 2,000,000 such as those with CTFA names PEG-200, PEG-400, PEG-600, PEG-1000, PEG-2M, PEG-7M, PEG-14M, PEG-45M and mixtures thereof.

iii. Cationic Deposition Polymers

The hair care composition may further comprise a cationic deposition polymer. Any known natural or synthetic cationic deposition polymer can be used herein. Examples include those polymers disclosed in U.S. Pat. No. 6,649,155; U.S. Patent Application Publication Nos. 2008/0317698;

2008/0206355; and 2006/0099167, which are incorporated herein by reference in their entirety.

The cationic deposition polymer is included in the composition at a level from about 0.01 wt % to about 2 wt %, in one embodiment from about 1.5 wt % to about 1.9 wt %, in another embodiment from about 1.8 wt % to about 2.0 wt %.

The cationic deposition polymer is a water soluble polymer with a charge density from about 0.5 milliequivalents per gram to about 12 milliequivalents per gram. The cationic deposition polymer used in the composition has a molecular weight of about 100,000 Daltons to about 5,000,000 Daltons. The cationic deposition polymer is a low charge density cationic polymer.

In one embodiment, the cationic deposition polymer is a synthetic cationic deposition polymer. A variety of synthetic cationic deposition polymers can be used including mono- and di-alkyl chain cationic surfactants. In one embodiment, mono-alkyl chain cationic surfactants are chosen including, for example, mono-alkyl quaternary ammonium salts and mono-alkyl amines. In another embodiment, di-alkyl chain cationic surfactants are used and include, for example, dialkyl (14-18) dimethyl ammonium chloride, ditallow alkyl dimethyl ammonium chloride, dihydrogenated tallow alkyl dimethyl ammonium chloride, distearyl dimethyl ammonium chloride, dicetyl dimethyl ammonium chloride, and mixtures thereof.

In another embodiment, the cationic deposition polymer is a naturally derived cationic polymer. The term, "naturally derived cationic polymer" as used herein, refers to cationic deposition polymers which are obtained from natural sources. The natural sources may be polysaccharide polymers. Therefore, the naturally derived cationic polymer may be selected from the group comprising starches, guar, cellulose, Cassia, locust bean, Konjac, Tara, galactomannan, tapioca, and synthetic polymers. In a further embodiment, cationic deposition polymers are selected from Mirapol® 100S (Rhodia), Jaguar® C17, polyDADMAC, Tapioca starch (Akzo), Triquat™, and mixtures thereof.

d. Anionic Emulsifiers

A variety of anionic emulsifiers can be used in the hair care composition as described below. The anionic emulsifiers include, by way of illustrating and not limitation, water-soluble salts of alkyl sulfates, alkyl ether sulfates, alkyl isothionates, alkyl carboxylates, alkyl sulfosuccinates, alkyl succinamates, alkyl sulfate salts such as sodium dodecyl sulfate, alkyl sarcosinates, alkyl derivatives of protein hydrolyzates, acyl aspartates, alkyl or alkyl ether or alkylaryl ether phosphate esters, sodium dodecyl sulphate, phospholipids or lecithin, or soaps, sodium, potassium or ammonium stearate, oleate or palmitate, alkylarylsulfonic acid salts such as sodium dodecylbenzenesulfonate, sodium dialkylsulfosuccinates, dioctyl sulfosuccinate, sodium dilaurylsulfosuccinate, poly(styrene sulfonate) sodium salt, isobutylene-maleic anhydride copolymer, gum arabic, sodium alginate, carboxymethylcellulose, cellulose sulfate and pectin, poly(styrene sulfonate), isobutylene-maleic anhydride copolymer, gum arabic, carrageenan, sodium alginate, pectic acid, tragacanth gum, almond gum and agar; semi-synthetic polymers such as carboxymethyl cellulose, sulfated cellulose, sulfated methylcellulose, carboxymethyl starch, phosphated starch, lignin sulfonic acid; and synthetic polymers such as maleic anhydride copolymers (including hydrolyzates thereof), polyacrylic acid, polymethacrylic acid, acrylic acid butyl acrylate copolymer or crotonic acid homopolymers and copolymers, vinylbenzenesulfonic acid or 2-acrylamido-2-methylpropanesulfonic acid homopolymers and copolymers, and partial amide or partial ester of such polymers and copolymers, carboxymodified polyvinyl alcohol, sulfonic acid-modified polyvinyl alcohol and phosphoric acid-modified polyvinyl alcohol, phosphated or sulfated tristyrylphenol ethoxylates.

In addition, anionic emulsifiers that have acrylate functionality may also be used in the instant shampoo compositions. Anionic emulsifiers useful herein include, but aren't limited to: poly(meth)acrylic acid; copolymers of (meth) acrylic acids and its (meth)acrylates with C1-22 alkyl, C1-C8 alkyl, butyl; copolymers of (meth)acrylic acids and (meth)acrylamide; Carboxyvinylpolymer; acrylate copolymers such as Acrylate/C10-30 alkyl acrylate crosspolymer, Acrylic acid/vinyl ester copolymer/Acrylates/Vinyl Isodecanoate crosspolymer, Acrylates/Palmeth-25 Acrylate copolymer, Acrylate/Steareth-20 Itaconate copolymer, and Acrylate/Celeth-20 Itaconate copolymer; Polystyrene sulphonate, copolymers of methacrylic acid and acrylamidomethylpropane sulfonic acid, and copolymers of acrylic acid and acrylamidomethylpropane sulfonic acid; carboxymethylcellulose; carboxy guar; copolymers of ethylene and maleic acid; and acrylate silicone polymer. Neutralizing agents may be included to neutralize the anionic emulsifiers herein. Non-limiting examples of such neutralizing agents include sodium hydroxide, potassium hydroxide, ammonium hydroxide, monoethanolamine, diethanolamine, triethanolamine, diisopropanolamine, aminomethylpropanol, tromethamine, tetrahydroxypropyl ethylenediamine, and mixtures thereof. Commercially available anionic emulsifiers include, for example, Carbomer supplied from Noveon under the tradename Carbopol 981 and Carbopol 980; Acrylates/C10-30 Alkyl Acrylate Crosspolymer having tradenames Pemulen TR-1, Pemulen TR-2, Carbopol 1342, Carbopol 1382, and Carbopol ETD 2020, all available from Noveon; sodium carboxymethylcellulose supplied from Hercules as CMC series; and Acrylate copolymer having a tradename Capigel supplied from Seppic. In another embodiment, anionic emulsifiers are carboxymethylcelluloses.

e. Benefit Agents

The benefit agents comprise a material selected from the group consisting of anti-dandruff agents; perfumes; brighteners; enzymes; perfumes; sensates in one aspect a cooling agent; attractants, anti-bacterial agents; dyes; pigments; bleaches; and mixtures thereof.

In one aspect said benefit agent may comprise an anti-dandruff agent. Such anti-dandruff particulate should be physically and chemically compatible with the essential components of the composition, and should not otherwise unduly impair product stability, aesthetics or performance.

According to an embodiment, the hair care composition comprises an anti-dandruff active, which may be an anti-dandruff active particulate. In an embodiment, the anti-dandruff active is selected from the group consisting of: pyridinethione salts; azoles, such as ketoconazole, econazole, and elubiol; selenium sulphide; particulate sulfur; keratolytic agents such as salicylic acid; and mixtures thereof. In an embodiment, the anti-dandruff particulate is a pyridinethione salt.

Pyridinethione particulates are suitable particulate anti-dandruff actives. In an embodiment, the anti-dandruff active is a 1-hydroxy-2-pyridinethione salt and is in particulate form. In an embodiment, the concentration of pyridinethione anti-dandruff particulate ranges from about 0.01 wt % to about 5 wt %, or from about 0.1 wt % to about 3 wt %, or from about 0.1 wt % to about 2 wt %. In an embodiment, the pyridinethione salts are those formed from heavy metals such as zinc, tin, cadmium, magnesium, aluminium and zirconium, generally zinc, typically the zinc salt of 1-hydroxy-2-pyridinethione (known as "zinc pyridinethione" or "ZPT"), commonly 1-hydroxy-2-pyridinethione salts in platelet particle form. In an embodiment, the 1-hydroxy-2-pyridinethione salts in platelet particle form have an average particle size of up to about 20 microns, or up to about 5 microns, or up to about 2.5 microns. Salts formed from other cations, such as sodium, may also be suitable. Pyridinethione anti-dandruff actives are described, for example, in U.S. Pat. Nos. 2,809,971; 3,236,733; 3,753,196; 3,761,418; 4,345,080; 4,323,683; 4,379,753; and 4,470,982.

In an embodiment, in addition to the anti-dandruff active selected from polyvalent metal salts of pyrithione, the composition further comprises one or more anti-fungal and/or anti-microbial actives. In an embodiment, the anti-microbial active is selected from the group consisting of: coal tar, sulfur, fcharcoal, whitfield's ointment, castellani's paint, aluminum chloride, gentian violet, octopirox (piroctone olamine), ciclopirox olamine, undecylenic acid and its metal salts, potassium permanganate, selenium sulphide, sodium thiosulfate, propylene glycol, oil of bitter orange, urea preparations, griseofulvin, 8-hydroxyquinoline clioquinol, thiabendazole, thiocarbamates, haloprogin, polyenes, hydroxypyridone, morpholine, benzylamine, allylamines (such as terbinafine), tea tree oil, clove leaf oil, coriander, palmarosa, berberine, thyme red, cinnamon oil, cinnamic aldehyde, citronellic acid, hinokitiol, ichthyol pale, Sensiva SC-50, Elestab HP-100, azelaic acid, lyticase, iodopropynyl butylcarbamate (IPBC), isothiazalinones such as octyl isothiazalinone, and azoles, and mixtures thereof. In an embodiment, the anti-microbial is selected from the group consisting of: itraconazole, ketoconazole, selenium sulphide, coal tar, and mixtures thereof.

In an embodiment, the azole anti-microbials is an imidazole selected from the group consisting of: benzimidazole, benzothiazole, bifonazole, butoconazole nitrate, climbazole, clotrimazole, croconazole, eberconazole, econazole, elubiol, fenticonazole, fluconazole, flutrimazole, isoconazole, ketoconazole, lanoconazole, metronidazole, miconazole, neticonazole, omoconazole, oxiconazole nitrate, sertaconazole, sulconazole nitrate, tioconazole, thiazole, and mixtures thereof, or the azole anti-microbials is a triazole selected from the group consisting of: terconazole, itraconazole, and mixtures thereof. When present in the hair care composition, the azole anti-microbial active is included in an amount of from about 0.01 wt % to about 5 wt %, or from about 0.1 wt % to about 3 wt %, or from about 0.3 wt % to about 2 wt %. In an embodiment, the azole anti-microbial active is ketoconazole. In an embodiment, the sole anti-microbial active is ketoconazole.

Embodiments of the hair care composition may also comprise a combination of anti-microbial actives. In an embodiment, the combination of anti-microbial active is selected from the group of combinations consisting of: octopirox and zinc pyrithione, pine tar and sulfur, salicylic acid and zinc pyrithione, salicylic acid and elubiol, zinc pyrithione and elubiol, zinc pyrithione and climbazole, octopirox and climbazole, salicylic acid and octopirox, and mixtures thereof.

In an embodiment, the composition comprises an effective amount of a zinc-containing layered material. In an embodiment, the composition comprises from about 0.001 wt % to about 10 wt %, or from about 0.01 wt % to about 7 wt %, or from about 0.1 wt % to about 5 wt % of a zinc-containing layered material, by total weight of the composition.

Zinc-containing layered materials may be those with crystal growth primarily occurring in two dimensions. It is conventional to describe layer structures as not only those in which all the atoms are incorporated in well-defined layers, but also those in which there are ions or molecules between the layers, called gallery ions (A. F. Wells "Structural Inorganic Chemistry" Clarendon Press, 1975). Zinc-containing layered materials (ZLMs) may have zinc incorporated in the layers and/or be components of the gallery ions. The following classes of ZLMs represent relatively common examples of the general category and are not intended to be limiting as to the broader scope of materials which fit this definition.

Many ZLMs occur naturally as minerals. In an embodiment, the ZLM is selected from the group consisting of: hydrozincite (zinc carbonate hydroxide), aurichalcite (zinc copper carbonate hydroxide), rosasite (copper zinc carbonate hydroxide), and mixtures thereof. Related minerals that are zinc-containing may also be included in the composition. Natural ZLMs can also occur wherein anionic layer species such as clay-type minerals (e.g., phyllosilicates) contain ion-exchanged zinc gallery ions. All of these natural materials can also be obtained synthetically or formed in situ in a composition or during a production process.

Another common class of ZLMs, which are often, but not always, synthetic, is layered double hydroxides. In an embodiment, the ZLM is a layered double hydroxide conforming to the formula $[M^{2+}_{1-x}M^{3+}_{x}(OH)_2]^{x+}A^{m-}_{x/m} \cdot nH_2O$ wherein some or all of the divalent ions ($M^{2+}$) are zinc ions (Crepaldi, E L, Pava, P C, Tronto, J, Valim, J B *J. Colloid Interfac. Sci.* 2002, 248, 429-42).

Yet another class of ZLMs can be prepared called hydroxy double salts (Morioka, H., Tagaya, H., Karasu, M, Kadokawa, J, Chiba, K *Inorg. Chem.* 1999, 38, 4211-6). In an embodiment, the ZLM is a hydroxy double salt conforming to the formula $[M^{2+}_{1-x}M^{2+}_{1+x}(OH)_{3(1-y)}]^{+}A^{n-}_{(1=3y)/n} \cdot nH_2O$ where the two metal ions ($M^{2+}$) may be the same or different. If they are the same and represented by zinc, the formula simplifies to $[Zn_{1+x}(OH)_2]^{2x+}2x\, A^- \cdot nH_2O$. This latter formula represents (where x=0.4) materials such as zinc hydroxychloride and zinc hydroxynitrate. In an embodiment, the ZLM is zinc hydroxychloride and/or zinc hydroxynitrate. These are related to hydrozincite as well wherein a divalent anion replaced the monovalent anion. These materials can also be formed in situ in a composition or in or during a production process.

In embodiments having a zinc-containing layered material and a pyrithione or polyvalent metal salt of pyrithione, the ratio of zinc-containing layered material to pyrithione or a polyvalent metal salt of pyrithione is from about 5:100 to about 10:1, or from about 2:10 to about 5:1, or from about 1:2 to about 3:1.

The on-scalp deposition of the anti-dandruff active is at least about 1 microgram/cm². The on-scalp deposition of the anti-dandruff active is important in view of ensuring that the anti-dandruff active reaches the scalp where it is able to perform its function. In an embodiment, the deposition of the anti-dandruff active on the scalp is at least about 1.5 microgram/cm², or at least about 2.5 microgram/cm², or at least about 3 microgram/cm², or at least about 4 microgram/cm², or at least about 6 microgram/cm², or at least about 7 microgram/cm², or at least about 8 microgram/cm², or at least about 8 microgram/cm², or at least about 10 microgram/cm². The on-scalp deposition of the anti-dandruff active is measured by having the hair of individuals washed with a composition comprising an anti-dandruff active, for example a composition pursuant to the hair care composition, by trained a cosmetician according to a conventional washing protocol. The hair is then parted on an area of the scalp to allow an open-ended glass cylinder to be held on the surface while an aliquot of an extraction solution is added and agitated prior to recovery and analytical determination of anti-dandruff active content by conventional methodology, such as HPLC.

Data

To test how well a chelant performs, a calcium dissolution assay can be performed. A calcium dissolution assay can simulate how well a particular hair care composition may be able to remove calcium fatty carboxylate salts from the hair. Unless otherwise mentioned, the following procedure may be used to determine how much calcium stearate can dissolve in particular composition: (1) Preparing a solution with 10% of an anionic surfactant by weight of the hair care composition and 1% of the selected chelant by weight of the hair care composition; (2) Adjusting the pH of the solution to the level of interest; (3) Adding calcium stearate powder to the solution (100 mg); (4) Shaking the mixture for 2 hours at 700 rpm; (5) Filtering the solution to remove any undissolved solids with a 0.2 μm filter; and (6) Performing gas chromatography analysis on the filtrate to measure level of dissolved calcium stearate. Unless otherwise mentioned or altered, the selected anionic surfactant is sodium laureth sulphate (SLE1S) and the pH value is 6.

Table 2 displays an experiment where the composition of the anionic surfactant and chelant are modified while the pH is held constant. A composition with no surfactant, but 2 wt % of the chelant HEDP, is able to dissolve calcium stearate. Similarly, a composition with 15 wt % of the anionic surfactant SLE1S, but no chelant, is not able to effectively dissolve calcium stearate. However, a composition which includes SLE1S (15 wt %) and a calcium chelant (HEDP 2 wt %) is able to effectively dissolve and remove calcium stearate.

TABLE 2

Chelation Performance

| Surfactant (wt %) | Chelant (wt %) | Calcium Stearate Dissolved (ppm) |
|---|---|---|
| SLE1S 0% | HEDP 2% | 0 |
| SLE1S 15% | HEDP 0% | 595 |
| SLE1S 15% | HEDP 2% | 3570 |

Table 3 screens a series of chelants for their ability to chelate and remove or solubilize calcium stearate. In this table, the composition includes 1 wt % of the selected chelant, 10 wt % of the anionic surfactant SLE1S, and a pH of 6. Table 3 lists aminocarboxylic acid-based chelants. For example, DTPA can dissolve at least 3775 ppm of calcium stearate, but can only remove less than 1% of copper based salts. This indicates that the careful selection of a chelant and a surfactant can allow for the removal of a calcium fatty carboxylate salt. On the other hand, EDDS (ethylenediamine-N,N'-disuccinic acid) can only dissolve up to 542 ppm of calcium stearate, but is moderately effective at dissolving copper based salts (32%). A chelant that can also chelate to copper ions may be less effective at chelating calcium ions. Copper and calcium chelation can be a competitive process. Table 3 indicates that not every chelant can be selected to effectively dissolve and remove calcium fatty carboylate salts.

TABLE 3

Aminocarboxylic acid chelants

| Chelant | Ca Binding Constant | % Copper Removal | Proton Available at pH 6 | Calcium Stearate Dissolved (ppm) |
|---|---|---|---|---|
| MGDA | 7.0 | — | Yes | 4172 |
| EDTA | 10.2 | — | Yes | 4157 |
| HEDTA | 8.1 | — | Yes | 4068 |
| DTPA | 9.9 | <1% | Yes | 3775 |
| ADA | 4.0 | — | Yes | 3222 |
| HIDA | 4.7 | 33% | Yes | 1013 |
| GLDA | 5.9 | — | Yes | 917 |
| NaLAA | — | — | Yes | 796 |
| CADA | — | — | Yes | 786 |
| IDA | 2.6 | 39% | Yes | 641 |
| Histidine | 1.2 | 55% | Yes | 195 |
| Glycine | 1.1 | 33% | Yes | 193 |

Table 4 displays a series of phosphorous containing chelants. In this table, the composition includes 1 wt % of the selected chelant, 10 wt % of the anionic surfactant SLE1S, and a pH of 6. Table 4 shows a similar trend where compounds that are good copper chelators show poor calcium binding ability. For example, HEDP can dissolve calcium stearate at a concentration of 1992 ppm, but can only remove 5% of copper ions. Phytic acid can only dissolve calcium stearate at a concentration of 819 ppm, but can remove up to 20% of copper ions.

TABLE 4

Phosphorous Containing Chelants

| Chelant | Ca Binding Constant | % Copper Removal | Proton Available at pH 6 | Calcium Stearate Dissolved (ppm) |
|---|---|---|---|---|
| Pyrophosphoric Acid | 5.4 | — | Yes | 3377 |
| HEDP | 5.5 | 5% | Yes | 1992 |
| Aledronic Acid | — | — | Yes | 1834 |
| DTPMP | 5.4 | 2% | Yes | 1555 |
| Neridronic Acid | — | — | Yes | 1207 |
| Phytic Acid | — | 20% | Yes | 819 |
| D2HEPA | — | — | No | 362 |

Table 5 displays a series of heterocyclic and other ring containing chelants. In this table, the composition includes 1 wt % of the selected chelant, 10 wt % of the anionic surfactant SLE1S, and a pH of 6. For example, a composition including HPNO can dissolve at least 2640 ppm of calcium stearate.

TABLE 5

Heterocyclic and other ring containing chelants

| Chelant | Ca Binding Constant | % Copper Removal | Proton Available at pH 6 | Calcium Stearate Dissolved (ppm) |
|---|---|---|---|---|
| HPNO | — | 26% | Yes | 2640 |
| Hinokitiol | 2.8 | 20% | Yes | 1238 |
| Octopirox | — | — | Yes | 1280 |
| Picolinic Acid | 1.8 | 50% | No | 874 |
| Pyrthione | — | — | No | 704 |
| Deferriprone | — | — | Yes | 514 |

Table 6 displays a study of the level of chelant that can be included in a hair care composition. In this table, the composition includes 10 wt % of the anionic surfactant SLE1S and a pH of 6, but the wt % of the chelant is varied. The amount of calcium stearate dissolved increases with an increasing wt % of DTPA.

TABLE 6

Chelant loading

| Chelant | Wt % of Composition | Calcium Stearate Dissolved (ppm) |
|---|---|---|
| DTPA | 1.0 | 3485 |
| DTPA | 0.6 | 2753 |
| DTPA | 0.3 | 1921 |
| DTPA | 0.0 | 600 |

Table 7 displays a study of the level of chelant that can be included in a hair care composition. In this table, the composition includes 10 wt % of the anionic surfactant SLE1S and a pH of 6, but the wt % of the chelant is varied. The amount of calcium stearate dissolved increases with an increasing wt % of HEDP.

TABLE 7

Chelant loading

| Chelant | Wt % of Composition | Calcium Stearate Dissolved (ppm) |
|---|---|---|
| HEDP | 2.0 | 5032 |
| HEDP | 1.0 | 1853 |
| HEDP | 0.6 | 1421 |
| HEDP | 0.3 | 794 |
| HEDP | 0.0 | 110 |

Table 8 displays the effect of pH on the removal or dissolution of calcium stearate. In this table, the composition includes 1 wt % of the selected chelant and 10 wt % of the anionic surfactant SLE1S, but the pH of the composition is modified. DTPA shows a consistent ability to dissolve calcium stearate at a pH of from about 4 to about 7. However, citric acid and succinic acid only are able to minimally dissolve calcium stearate at pH 4 and pH 5. At pH 6 and pH 7, citric acid and succinic acid are not able to dissolve calcium stearate, possibly due to the pKa of each compound.

TABLE 8

Effect of pH

| Chelant | Wt % of Composition | pH | Calcium Stearate Dissolved (ppm) |
|---|---|---|---|
| DTPA | 1.0 | 4 | 4257 |
| DTPA | 1.0 | 5 | 3870 |
| DTPA | 1.0 | 6 | 3775 |
| DTPA | 1.0 | 7 | 3860 |
| Succinic Acid | 1.0 | 4 | 3382 |
| Succinic Acid | 1.0 | 5 | 4292 |
| Succinic Acid | 1.0 | 6 | 981 |
| Succinic Acid | 1.0 | 7 | 220 |
| Citric Acid | 1.0 | 4 | 3197 |
| Citric Acid | 1.0 | 5 | 2983 |
| Citric Acid | 1.0 | 6 | 1102 |
| Citric Acid | 1.0 | 7 | 442 |

Table 9 shows the effect of the addition of a zwitterionic surfactant upon the addition of greater percentages of a zwitterionic surfactant, more calcium stearate is dissolved.

TABLE 9

Zwitterionic Surfactant

| HEDP | Sodium Laureth Sulfate | Zwitterionic Surfactant | Calcium Stearate Dissolved (ppm) |
|---|---|---|---|
| 1% | 10% | 0% | 1588 |
| 1% | 9% | 1% | 1514 |
| 1% | 7% | 3% | 2230 |
| 1% | 5% | 5% | 2387 |

Table 10 shows the effect of the addition of a hydrotrope on the dissolution and removal of calcium fatty carboxylate salts. In this table, the composition includes 1 wt % of the selected chelant, 10 wt % of the anionic surfactant SLE1S, and a pH of 6. The addition of a hydrotrope, sodium xylenesulfonate (SXS) improves the compositions ability to dissolve calcium stearate.

TABLE 10

Hydrotrope

| HEDP | Hydrotrope (SXS) | Calcium Stearate Dissolved (ppm) |
|---|---|---|
| 1% | 0% | 1613 |
| 1% | 2.8% | 4114 |

Examples

The following examples illustrate embodiments of the hair care composition described herein. The exemplified compositions can be prepared by conventional formulation and mixing techniques. It will be appreciated that other modifications of the hair care composition within the skill of those in the shampoo formulation art can be undertaken without departing from the spirit and scope of this invention. All parts, percentages, and ratios herein are by weight unless otherwise specified. Some components may come from suppliers as dilute solutions. The amount stated reflects the weight percent of the active material, unless otherwise specified.

The following are non-limiting examples of shampoo compositions either encompassed by embodiments of the hair care composition or comparative.

TABLE 11

| Ingredient | Ex. A1 | Ex. A2 | Ex. A3 | Ex. A4 | Ex. A5 | Ex. A6 | Ex. A7 |
|---|---|---|---|---|---|---|---|
| HEDP | 0.2 | 0.5 | 1 | 1 | 2 | 5 | 10 |
| SLE1S | 10 | 10 | 10 | 10 | 10 | 10 | 10 |
| SXS | 2.8 | 2.8 | 2.8 | 2.8 | 2.8 | 2.8 | 2.8 |
| CapB | 2 | 2 | 2 | 1 | 2 | 2 | 2 |
| Carrier* | Q.S. to 100 | Q.S. to 100 | Q.S. to 100 | Q.S. to 100 | Q.S. to 100 | Q.S. to 100 | Q.S. to 100 |

*Carrier may include other optional or minor ingredients

TABLE 12

| Ingredient | Ex. B1 | Ex. B2 | Ex. B3 | Ex. B4 | Ex. B5 | Ex. B6 | Ex. B7 |
|---|---|---|---|---|---|---|---|
| Chelant at 1 wt % | DTPA | HEDTA | MGDA | HIDA | HPNO | DTPMP | ADA |

TABLE 12-continued

| Ingredient | Ex. B1 | Ex. B2 | Ex. B3 | Ex. B4 | Ex. B5 | Ex. B6 | Ex. B7 |
|---|---|---|---|---|---|---|---|
| SLE1S | 10 | 10 | 10 | 10 | 10 | 10 | 10 |
| SXS | 2.8 | 2.8 | 2.8 | 2.8 | 2.8 | 2.8 | 2.8 |
| Cap B | 2 | 2 | 2 | 2 | 2 | 2 | 2 |
| Carrier* | Q.S. to 100 | Q.S. to 100 | Q.S. to 100 | Q.S. to 100 | Q.S. to 100 | Q.S. to 100 | Q.S. to 100 |

*Carrier may include other optional or minor ingredients

TABLE 13

| Ingredient | Ex. C1 | Ex. C2 | Ex. C3 |
|---|---|---|---|
| Sodium lauryl ether sulfate (SLE1S) (1) | 14 | 14 | 14 |
| Cocamidopropyl betaine (Cap B) (2) | 2 | 2 | 2 |
| Stearyl alcohol (3)* | 1.29 | 1.29 | 1.29 |
| Cetyl alcohol (4)* | 0.71 | 0.71 | 0.71 |
| Silicone (dimethicone/dimethiconol) (5) | 1 | 1 | 1 |
| Hydrogenated castor oil (trihydroxysterin) (6) | 0.1 | 0.1 | 0.1 |
| Guar hydroxypropyltrimonium chloride (7) | 0.15 | 0.15 | 0.15 |
| Synthetic cationic polymer DADMAC (8) | 0.1 | 0.1 | 0.1 |
| Chelant | 1 (HEDP) | 2 (HEDP) | 1 (DTPA) |
| Water-USP purified & minors | Q.S. to 100 | Q.S. to 100 | Q.S. to 100 |

(1) Sodium Laureth-1 Sulfate from the Stepan Company
(2) Amphosol HCA from Stepan Company
(3) CO 1895 from Procter & Gamble
(4) CO 1695 from Procter & Gamble
(5) Silicone Belsil DM 5500 from Wacker Chemical Corp.
(6) Thixcin R from Elements
(7) Jaguar C500 from Rhodia
(8) Poly (Dially) Dimethyl Ammonium Chloride from Rhodia
*Fatty alcohol is added as part of the Gel

TABLE 14

| Ingredient | Ex. D1 | Ex. D2 | Ex. D3 |
|---|---|---|---|
| Sodium lauryl sulfate (SLS) (1) | 1.5 | 1.5 | 1.5 |
| Sodium lauryl ether sulfate (SLE1S) (2) | 12 | 12 | 12 |
| Cocamidopropyl betaine (CapB) (3) | 2 | 2 | 2 |
| Silicone (dimethicone/dimethiconol) (4) | 1 | 1 | 1 |
| Hydrogenated castor oil (trihydroxysterin) (5) | 0.1 | 0.1 | 0.1 |
| Guar hydroxypropyltrimonium chloride (6) | 0.25 | 0.25 | 0.25 |
| Zinc pyrithione (7) | 1 | 1 | 1 |
| Zinc carbonate (8) | 1.61 | 1.61 | 1.61 |
| Chelant | 1 (HEDP) | 2 (HEDP) | 1 (DTPA) |
| Water-USP purified & minors | Q.S. to 100 | Q.S. to 100 | Q.S. to 100 |

(1) Sodium lauryl sulfate from Stepan Company
(2) Sodium laureth-1 sulfate from the Stepan Company
(3) Amphosol HCA from Stepan Company
(4) Silicone belsil DM 5500 from Wacker Chemical Corp.
(5) Thixcin R from Elements
(6) Jaguar C500 from Rhodia
(7) ZPT from Lonza Chemical
(8) Zinc carbonate from Bruggeman Group

TABLE 15

| Ingredient | Ex. E1 | Ex. E2 | Ex. E3 |
|---|---|---|---|
| Sodium Laureth-1 Sulfate | 12.91 | 12.91 | 12.91 |
| Cocamidopropyl Betaine | 2.00 | 2.00 | 2.00 |
| Tetrasodium EDTA Tetrahydrate | 0.16 | 0.16 | 0.16 |
| Sodium Benzoate | 0.25 | 0.25 | 0.25 |
| Ethyleneglycol distearate | 0.15 | 0.15 | 0.15 |
| Guar Hydroxypropyltrimonium Chloride | 0.25 | 0.25 | 0.25 |
| Dimethicone | 1.00 | 1.00 | 1.00 |
| Perfume | 0.80 | 0.80 | 0.80 |
| Trisodium Ethylenediamine Disuccinate | 0.26 | 0.26 | 0.26 |
| HEDP (1) | 0.50 | 1.00 | 2.00 |
| Sodium Chloride | Adjust for viscosity | Adjust for viscosity | Adjust for viscosity |
| Sodium Xylenesulfonate | 2.80 | 2.80 | 2.80 |
| Citric Acid | Adjust for pH | Adjust for pH | Adjust for pH |
| Sodium Citrate | Adjust for pH | Adjust for pH | Adjust for pH |
| Kathon CG | 0.03 | 0.03 | 0.03 |
| Distilled Water | Q.S. to 100% | Q.S. to 100% | Q.S. to 100% |

(1) Any suitable calcium chelant can be substituted

TABLE 16

| Ingredient | Ex. F1 | Ex. F2 | Ex. F3 |
|---|---|---|---|
| Sodium Laureth-1 Sulfate | 12.37 | 12.37 | 12.37 |
| Cocamide opropyl Betaine High pH Bulk | 2.58 | 2.58 | 2.58 |
| Dimethiconol (in TEA-Dodecylbenzesulfonate, Laureth-23) emulson | 0.52 | 0.52 | 0.52 |
| Sodium Benzoate | 0.25 | 0.25 | 0.25 |
| Glycerin | 0.06 | 0.06 | 0.06 |
| Guar Hydroxypropyltrimonium Chloride | 0.15 | 0.15 | 0.15 |
| Polyquaternium-10 | 0.21 | 0.21 | 0.21 |
| Sodium Xylenesulfonate | 2.80 | 2.80 | 2.80 |
| Sodium chloride | Viscosity adjustment | Viscosity adjustment | Viscosity adjustment |
| Citric acid | pH adjustment | pH adjustment | pH adjustment |
| Tetrasodium EDTA | 0.16 | 0.16 | 0.16 |
| HEDP (1) | 0.50 | 1.00 | 2.00 |

TABLE 16-continued

| Ingredient | Ex. F1 | Ex. F2 | Ex. F3 |
| --- | --- | --- | --- |
| Kathon CG | 0.03 | 0.03 | 0.03 |
| Perfume | 0.82 | 0.82 | 0.82 |
| Water | Q.S. to 100 wt % | Q.S. to 100 wt % | Q.S. to 100 wt % |

(1) Any suitable calcium chelant can be substituted

TABLE 17

| Ingredient | Ex. G1 | Ex. G2 | Ex. G3 |
| --- | --- | --- | --- |
| Sodium Laureth-1 Sulfate | 10.50 | 10.50 | 10.50 |
| Sodium Lauryl Sulfate | 1.50 | 1.50 | 1.50 |
| Cocoamidopropyl betaine | 1.00 | 1.00 | 1.00 |
| Sodium Benzoate | 0.25 | 0.25 | 0.25 |
| Citric acid | 1.00 | 1.00 | 1.00 |
| Kathon CG | 0.03 | 0.03 | 0.03 |
| NaCl | Viscosity adjustment | Viscosity adjustment | Viscosity adjustment |
| Disodium EDTA | 0.16 | 0.16 | 0.16 |
| HEDP (1) | 0.50 | 1.00 | 2.00 |
| Water | Q.S. to 100 wt % | Q.S. to 100 wt % | Q.S. to 100 wt % |

(1) Any suitable calcium chelant can be substituted

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the hair care composition have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for improving hair shine and/or reducing hair damage by removing calcium fatty carboxylate salts from hair comprising:
    a) applying a shampoo composition to the hair, the shampoo composition comprising:
        i) about 0.2% to about 2% of a calcium chelant selected from the group consisting of diethylenetriaminepentaacetic acid (DTPA) etidronic acid and mixtures thereof, and
        ii) about 5% to about 15% of an anionic surfactant by weight of the shampoo composition, wherein the anionic surfactant is selected from the group consisting of sodium lauryl sulfate, sodium laureth sulfate, and combinations thereof,
        iii) about 0.1% to about 5% of a hydrotrope by weight of the shampoo composition, and
        iv) about 45% to about 95% of a carrier by weight of the shampoo composition, wherein the pH of the shampoo composition is from about 4 to about 6;
    b) dissolving more than 1013 ppm calcium stearate; and
    c) rinsing the shampoo composition from the hair, thereby removing the calcium fatty carboxylate salts from the hair, wherein the hair shine is improved and/or the hair damage is reduced.

2. The method of claim 1, wherein the shampoo composition comprises from about 0.5% to about 5% of a zwitterionic surfactant, by weight of the shampoo composition.

3. The method of claim 2, wherein the shampoo composition comprises from about 0.75% to about 2% of the zwitterionic surfactant, by weight of the shampoo composition.

4. The method of claim 2, wherein the zwitterionic surfactant is a betaine derivative.

5. The method of claim 1, wherein the shampoo composition comprises from about 0.2% to about 3% of the hydrotrope by weight of the shampoo composition.

6. The method of claim 1, wherein the hydrotrope is selected from the group consisting of salts of xylene sulfonic acid, toluene sulfonic acid, cumene sulfonic acid, and mixtures thereof.

7. The method of claim 1, further comprising a gel network, wherein the gel network comprises a fatty alcohol and a gel network surfactant.

8. The method of claim 1, wherein the carrier is selected from the group consisting of water, an organic solvent, and mixtures thereof.

9. The method of claim 1, further comprising an anti-dandruff active.

10. A method for improving hair shine and/or reducing hair damage by removing calcium fatty carboxylate salts from hair comprising:
    a) applying a shampoo composition to the hair, comprising:
        i) about 0.5% to about 1.5% etidronic acid, by weight,
        ii) about 5% to about 20% sodium laureth sulfate, by weight of the shampoo composition,
        iii) about 0.1% to about 3% of xylene sulfonic acid by weight of the shampoo composition,
        iv) about 45% to about 95% of water, by weight of the shampoo composition, wherein the pH of the shampoo composition is about 5 to about 6;
    b) dissolving about 794 ppm to about 5032 ppm calcium stearate; and
    c) rinsing the shampoo composition from the hair, thereby removing the calcium fatty carboxylate salts from the hair.

11. The method of claim 10, wherein the shampoo further comprises 1% to 12% of a zwitterionic surfactant selected from the group consisting of cocamidoethyl betaine, cocamidopropylamine oxide, cocamidopropyl betaine, cocamidopropyl dimethylaminohydroxypropyl hydrolyzed collagen, cocamidopropyldimonium hydroxypropyl hydrolyzed collagen, cocamidopropyl hydroxysultaine, cocobetaineamido amphopropionate, coco-betaine, coco-hydroxysultaine, coco/oleamidopropyl betaine, coco-sultaine, lauramidopropyl betaine, lauryl betaine, lauryl hydroxysultaine, lauryl sultaine, and mixtures thereof.

\* \* \* \* \*